United States Patent [19]

Defaye et al.

[11] Patent Number: 5,118,804
[45] Date of Patent: Jun. 2, 1992

[54] PROCESS FOR PREPARING ALKYL-1-THIOGLYCOSIDES AND ALKYL-GLYCOSIDES, ANOMER MIXTURES THEREOF

[75] Inventors: Jacques Defaye; Andrée Gadelle, both of Saint Dismier, France; Christian Pedersen, Virum, Denmark

[73] Assignee: Beghin-Say, SA, Thumeries, France

[21] Appl. No.: 560,740

[22] Filed: Jul. 31, 1990

[30] Foreign Application Priority Data

Jul. 31, 1989 [FR] France .................. 89 10301

[51] Int. Cl.⁵ .................. C07H 1/00; C07H 15/00
[52] U.S. Cl. .................. 536/120; 536/18.5; 536/18.6; 536/17.5; 536/122; 536/124
[58] Field of Search .................. 536/120, 18.5, 18.6, 536/17.5, 122, 124

[56] References Cited

U.S. PATENT DOCUMENTS

| H619 | 4/1989 | McDaniel et al. ............... 536/18.6 |
| 2,563,884 | 8/1951 | Sugihara ............... 536/122 |
| 3,375,243 | 3/1968 | Nevin et al. ............... 536/18.6 |
| 3,839,318 | 10/1974 | Mansfield ............... 536/18.6 |
| 3,974,138 | 8/1976 | Lew ............... 536/18.6 |
| 4,223,129 | 9/1980 | Roth et al. ............... 536/18.6 |
| 4,683,297 | 7/1987 | Yanami et al. ............... 536/18.6 |
| 4,713,447 | 12/1987 | Letton ............... 536/124 |
| 4,721,780 | 1/1988 | McDaniel et al. ............... 536/120 |
| 4,820,692 | 4/1989 | Riscoe et al. ............... 536/122 |
| 4,957,904 | 9/1990 | Falk et al. ............... 536/17.5 |

FOREIGN PATENT DOCUMENTS 60-034913 2/1985 Japan .

*Primary Examiner*—Johnnie R. Brown
*Assistant Examiner*—Everett White
*Attorney, Agent, or Firm*—Breiner & Breiner

[57] ABSTRACT

A process for preparing alkykl-1-thio-$\alpha,\beta$-glycosides and alkyl glycosides is described. The glycosides are prepared from a saccharide selected from monosaccharides and reducible di- and oligo-saccharides. The saccharide is reacted with either a thiol to produce an alkyl-1-thio-$\alpha,\beta$-glycoside or an alcohol to produce an alkyl glycoside in the presence of the solvent and reagent poly-(hydrogen fluoride)-pyridinium. Novel alkyl-1-thio-$\alpha,\beta$-glycosides prepared by the process of the invention are characterized in that they are in the form of a mixture of $\alpha$ and $\beta$ anomers. The alkyl-1-thio-$\alpha,\beta$-glycosides having a long alkyl chain are useful as non-ionic detergents, in particular in the extraction of membrane proteins.

13 Claims, No Drawings

PROCESS FOR PREPARING ALKYL-1-THIOGLYCOSIDES AND ALKYL-GLYCOSIDES, ANOMER MIXTURES THEREOF

FIELD OF THE INVENTION

The present invention is directed to a new process for making alkyl-1-thioglycosides and alkyl glycosides. More specifically, the invention concerns an improved process for preparing alkyl-1-thioglycosides, in particular those having a long alkyl or fatty acid chain, and alkyl glycosides, in particular those having a long alkyl or fatty acid chain, by the respective reaction of a thiol or an alcohol with a saccharide selected from monosaccharides and reducible di- and oligo-saccharides. The reaction takes place in the presence of a poly-(hydrogen fluoride)-pyridinium solvent and reagent. The present invention is also directed to alkyl-1-thio-$\alpha,\beta$-glycosides which are mixtures of $\alpha$ and $\beta$-anomers obtained by the process of the present invention, and their use as nonionic detergents.

BACKGROUND OF INVENTION

Alkyl-1-thioglycosides having a long alkyl or fatty acid chain and their oxygenated analogs are known for their surfactant properties and are used as surfactants or detergents. An important characteristic of these families of glucide derivatives is the ability of the hydrophobic and hydrophilic functional groups therein to simultaneously combine on the same molecule. This characteristic allows these compounds to form monomolecular layers at the interfaces between immiscible solvents and micelles when the concentration of the micelles in solution exceeds a limit value known as the critical micelle concentration (CMC). This physical-chemical behavior is the cause of exceedingly significant, as well as diverse, applications of the surfactants as wetting agents, dispersants, emulsifiers, and, more generally, solubilizers. The surfactants also are known for their thermotropic and lysotropic properties of liquid crystals.

The alkyl glycosides having a fatty acid chain and alkyl-1-thioglycosides constitute an especially significant class of detergents because, being nonionic, their CMC and hence many of their desirable properties do not depend on the presence of a compensating ion. The generally high CMC value of these materials allows for easy and rapid elimination of the compounds by dialysis. These features in particular have led to their preferential use in biochemistry as solubilizers, in the extraction and reconstitution of membrane proteins, and their use as amphiphile derivatives which can act as a denaturant for complex and unstable biological structures. The fatty acid chain alkyl-1-thioglycosides also are of interest in relation to their alkyl glycoside analogs since the analogs are insensitive to most of the glycosidase enzymes which are present in biological media, as shown by the results published in *Biochem. J.*, 222 (1984) 829. Regarding the biochemical applications reported to date in the literature, only the 1,2-transanomers of the alkyl-1-thioglycosides have been put to use (see for instance *Chem. Pharm. Bull.*, 33, No. 2 (1985), 503).

Generally, alkyl-1-thioglycosides are prepared by reacting an alkyl halide with an o-acetylated 1-thioglycose, as disclosed in Japanese Patent No. 61-7288. Another method recently suggested (*Tetrahedron Lett.*, 29 (1988) 4293) makes use of the principle of the radical addition of an alkene onto this same derivative of 1-thioglycose in the presence of azobis-(isobutyronitrile). Such procedures, however, are time-consuming because they require at least four stages and employ costly reagents. Furthermore, these procedures lead solely to the 1,2-trans anomer of alkyl-1-thioglycopyranoside because the precursor acyl-1-thioglycose has the same configuration based on its synthesis. Accordingly, at this time only fatty acid chain alkyl-1-thioglycopyranosides of $\beta$-D anomerism in the series of glucopyranose, galactopyranose and xylopyranose have been described, or with regard to the $\alpha$-D form, mannopyranose.

The fatty acid chain alkyl glycosides are generally prepared by trans-acetylation in the presence of an acid catalyst in the manner as described in German Patent Application Nos. DE-A-1,905,523 and DE-A-1,943,689. The starting compounds are usually a lower glycoside alcohol or a mixture of a glycoside and a lower alcohol and a fatty alcohol. A related procedure to the Koenigs-Knorr reaction, which involves the action of a long chain alcohol on a peracetylated glycosyl halide in the presence of silver salts, has also been suggested by Koeltzow et al in *J. Am. Oil Chem Soc.*, 61 (1984) 1651. This latter procedure also results in the $\beta$ anomers of cellobiose, maltose and maltotriose.

Applicant's PCT application WO-A-8600906 describes a synthesis of fatty alcohol alkyl glycosides by reacting a fatty alcohol with an aldose, an aldoside or a polyaldoside in a solvent and reagent consisting of a mixture of dioxane/hydrogen fluoride or sulfur dioxide/hydrogen fluoride resulting in a yield of about 30%. This procedure, however, is not usable for synthesizing alkyl oligosaccharides because the reaction conditions result in fluorolysis of the oxygenated interoside bonds. Lower alcohol alkyl glycosides can be synthesized with good yields in the manner according to WO-A-8600906 by reacting an alcohol with an aldose, an aldoside or a polyaldoside in a solvent and reagent consisting of hydrogen fluoride. However, the quantity of alcohol used is high and the molar ratio of alcohol to the monosaccharide equivalent is advantageously about 20. Further, the lower alkyl oligosaccharides again are precluded for the aforementioned reasons.

OBJECTS OF THE INVENTION

An object of the present invention is to prepare alkyl-1-thio-$\alpha,\beta$-glycosides in a single stage process from either a monosaccharide, a disaccharide or an oligosaccharide.

Another object of the present invention is to prepare alkyl-oligosaccharides in a single stage.

Another object of the present invention is to prepare fatty acid chain alcohol alkyl glycosides in a single stage in a good yield from either a monosaccharide, disaccharide or an oligosaccharide.

Another object of the present invention is to prepare lower alcohol alkyl glycosides by reacting a saccharide with a slight excess of alcohol based on the stoichiometry of the compounds.

Another object of the invention is to use the mixtures of $\alpha$ and $\beta$ anomers of the alkyl glycosides and alkyl-1-thioglycosides as surfactants, in particular for extracting membrane proteins.

Other objects and advantages of the present invention are further elucidated in the description below.

BRIEF DESCRIPTION OF THE INVENTION

The present invention fulfills the objects of the invention by providing a process for preparing in a single stage alkyl-1-thio-α,β-glycosides and alkyl glycosides from a saccharide selected from monosaccharides and reducible di- and oligo-saccharides. The saccharide is reacted with a thiol, if an alkyl-1-thio-α,β-glycoside is to be produced, or an alcohol, if an alkyl glycoside is to be produced, in the presence the solvent and reagent poly-(hydrogen fluoride)-pyridinium. The resulting product is formed rapidly with an excellent yield and then subjected to extraction. The poly-(hydrogen fluoride)-pyridinium, which is also known as a hydrogen fluoride pyridinium reagent, is a commercial product, and can be prepared in a manner as described by Olah et al in J. Org. Chem., 44 (1979) 3872.

DESCRIPTION OF THE PRESENTLY PREFERRED EMBODIMENT

The process of the invention provides for the preparation in a single stage of fatty acid long chain alkyl glycosides, alkyl-1-thio-α,β-glycosides, thiol alkyl-1-thio-α, β-glycosides or lower alcohol alkyl glycosides from a monosaccharide or a reducible di- or oligo-saccharide.

Suitable monosaccharides include hexoses and pentoses. D-glucose and an amino-desoxy-hexose such as 2-acetamido-2-desoxy-D-glucose are preferred compounds due to their commercial availability. Suitable di- and oligo-saccharides which are preferred for the same reasons of availability are disaccharides such as cellobiose, lactose and maltose. Oligo-saccharides having a higher degree of polymerization and comprising up to ten or more repeating monosaccharide units are also usable provided that the final desired detergent properties are achieved.

When preparing the alkyl-1-thio-α,β-glycosides, the ratio of the thiol to saccharide reactants are optimally substantially equimolar when a monosaccharide is utilized. When a di- or oligo-saccharide is used, it has been found that an excess by about 1 mole of thiol based on the stoichiometry of the compounds results in a better reaction yield.

When preparing alkyl glycosides, preferably an excess up to 2 to 3 moles of the alcohol reactant per mole of the saccharide reactant is used.

The quantity utilized of the poly-(hydrogen fluoride)-pyridinium reagent and solvent is not critical and is only required to be present in an amount which provides for a homogeneous phase operation. While it is noted that no significant advantage is gained by increasing the quantity of the poly-(hydrogen fluoride)-pyridinium reagent and solvent beyond the amount needed to produce a homogeneous reaction medium, it is also noted that except for increasing material costs, no detriment results when the quantity of the solvent and reagent utilized is increased.

The process of the invention provides for the production of both long or fatty acid chain alkyl glycosides and alkyl-1-thio-α,β-glycosides from corresponding alcohols and thiols respectively. To produce long chain alkyl-1-thio-α,β-glycosides, a thiol reagent will preferably be a long chain thiol having from 5 to 20 carbon atoms although thiols having a larger number of carbon atoms can also be used. The selection of the thiol to be used is affected by the desired balance between the hydrophilic and lipophilic properties of the end product. Without implying any limitation, the mercaptans, 1-heptanethiol and 1-octanethiol, are preferred compounds for use in the process of the invention.

Generally, the alkyl-1-thio-α,β-glycosides form very rapidly. It has been found that an optimal yield is achieved when the reaction time is from approximately 30 mins. to 5 hours. The crude product obtained in the reaction following neutralization and extraction consists of a mixture of 1,2-cis and 1,2-trans anomers of the alkyl-1-thioglycopyranosides in differing proportions depending on the saccharide used. For D-glucose, this proportion is about 44% of the α anomer and 56% of the β anomer. A low proportion of the dithioacetal derivative of the monosaccharide used may also be formed. For example, the dithioacetal derivative is present in an amount of about 5% in the case of D-glucose in the conditions as set forth in Example 1 below. Generally, this contaminant is not troublesome and can be easily eliminated by crystallization.

The alkyl-1-thio-α,β-glycosides present in the form of a mixture of their α and β anomers made in accordance with the process of the present invention are novel. As described above, while for a particular alkyl-1-thioglycoside compound, the preparation of a single α anomer or a single β anomer has been described in the art, the preparation of the α and β anomers as a mixture has not been described in the art.

To make the fatty acid chain alkyl glycosides of the invention, the thiol utilized in the process described above is replaced by an alcohol corresponding to the fatty acid chain alkyl glycoside desired to be produced. Preferably, an excess of 2 to 3 moles of the alcohol reactant per mole of the saccharide reactant is used. Even though the yields of the fatty acid chain alkyl glycosides are generally less than the yields produced in preparing the alkyl-1-thio-α,β-glycosides, the yields of the process of the invention are higher than the yields obtained using the methods of the prior art. Additionally, the present invention can be used to produce alkyl oligosaccharides which prior to the present invention were not producible in a single stage process.

The process of preparing alkyl glycosides and alkyl-1-thio-α,β-glycosides from thiols and lower alcohols according to the present invention is also advantageous because of the slight amount of aglycone reactant present as evident from isotope tracing of the aglycone residue.

The critical micelle concentrations as measured according to the Tsuchiya and Saito method, J. Biochem., 96 (1984), 1593, are set forth in Table 1 for various fatty acid chain alkyl-1-thio-α,β-glycosides prepared according to the present invention.

TABLE 1

| Critical micelle concentrations (CMC) of alkyl-thio-α,β-glycosides made by the process of the invention. | |
|---|---|
| Alkyl-1-thioglycoside | CMC (mM) |
| 1-heptyl-1-thio-α,β-D-glucopyranoside | 4.1 |
| 1-octyl-1-thio-α,β-D-glucopyranoside | 3.0 |
| 1-octyl-1-thio-α,β-cellobioside | 0.2 |
| 1-octyl-1-thio-α,β-lactoside | 0.2 |
| 1-octyl-1-thio-α,β-maltoside | 0.2 |

In comparison, the CMC of 1-octyl-1-thio-β-D-glucopyranoside of the prior art mentioned in the literature is 9.0 mM (Chem. Pharm. Bull., 33 (1985), 503-8, S. Saito and T. Tsuchiya).

These CMC values allow the glycosides to be used as detergents in membrane protein extraction. For example, but without implying any limitation with regard to other uses, several alkyl-1-thio-α,β-glycosides prepared in the manner of the invention were used to extract membrane proteins from the bovine suprarenal cortex. The suprarenal cortex cells contain enzyme systems which cause steroidogenesis. These are membrane enzymes in the mitochondrions (cytochromes $P-450_{11\beta}$ and $P-450_{scc}$) and in the microsomes (cytochrome $P-450_{17\alpha}$). In conventionally used methods, they are optimally extracted in the presence of sodium cholate. However, the ionic nature of the sodium cholate detergent results in a greater denaturation rate of the enzymatic proteins as the contact time between the proteins and the sodium cholate is prolonged. Accordingly, and in particular, the sodium cholate detergent presents suprarenal cortex are prepared in the manner of M. Satre & P. V. Vignais (*Biochemistry*, 13 (1974) 2201). The membrane proteins are extracted by incubation in a suitable buffer containing 50 mM potassium phosphate, pH=7.4, 1 mM dithiothreitol, 1 mM EDTA, and 10 μM desoxycorticosterone. The respective concentrations of proteins and detergents are 20 and 15 mg/ml. Following incubation, the medium is centrifuged (100,000 g, 45 mins.) and the cytochromes P-450 are metered into the supernatant by recording the differential spectrum for the reduced form $Fe^{2+}$ and the complex $Fe^{2+}+CO$. Denaturation is estimated by the absorption difference measured at 450 nm (native form) and 420 nm (denatured form). Further, Table 2 shows for different commercial detergents, the comparative inactivation rates of the membrane proteins as a function of the detergent used.

TABLE 2

| Detergent | Inactivation rate | | Extraction rate | |
|---|---|---|---|---|
| | [after 1 h] | [after 2 h] | [after 1 h] | [after 2 h] |
| 1-heptyl-1-thio-α,β-D-glucopyranoside | 48 | 47 | 0 | 0 |
| 1-octyl-1-thio-α,β-D-glucopyranoside | 60 | 72 | 43 | 49 |
| 1-octyl-1-thio-β-D-glucopyranoside[a] | 18 | 91 | 0 | 48 |
| 1-octyl-β-D-glucopyranoside[a] | 100 | 100 | 0 | 0 |
| sodium cholate[b] | 94 | / | 0 | / |
| 1-heptyl-1-thio-α,β-lactoside | 30 | 50 | 0 | 0 |
| 1-octyl-1-thio-α,β-lactoside | 55 | 62 | 0 | 0 |
| 1-octyl-1-thio-α,β-cellobioside | 55 | 20 | 0 | 0 |
| 1-octyl-1-thio-α,β-maltoside | 48 | 94 | 0 | 21 |

[a]Commercial products of "ultra-pure" quality
[b]Commercial product of "ultra-pure" quality difficulties when used to reconstitute the lipid environment of these proteins.

The comparative extraction rates for the cytochromes $P-450_{11\beta}$ and $P-450_{scc}$, as set forth in Table 2 below, and $P-450_{17\alpha}$, as set forth in Table 3 below, in relation to commercial detergents, show that the alkyl-1-thio-α,β-glycosides prepared by the process of the present invention offer good extraction and reconstitution properties for these unstable proteins.

Tables 2 and 3 also show that the extraction yields and respective inactivation rates vary substantially depending on the particular proteins and detergents utilized. Generalizations, therefore, cannot be made at this time with respect to which detergents are suitable for a broad range of proteins in view of the present state of knowledge in the art. Accordingly, it appears that the extraction methods for membrane proteins remain largely empirical and that it is desirable to have available for use in extracting proteins the largest number possible of nonionic detergents at the lowest cost. This is one of the particular objects of the present invention.

Table 2 below shows the relative yields of extraction for the cytochromes $P-450_{11\beta}$ and $P-450_{scc}$ from the mitochondrions of the bovine suprarenal cortex when different detergents made by the process of the present invention are used. The mitochondrions of the bovine Table 3 shows the comparative yields of extraction of cytochrome $P-450_{17\alpha}$ from the bovine suprarenal cortex microsomes using different detergents made by the process of the present invention as well as different commercial detergents, and the comparative inactivation rates of the membrane proteins as a function of the particular detergent used. The extraction of cytochrome $P-450_{17\alpha}$ involved obtaining the bovine suprarenal cortex microsomes in the form of a button after 45 mins. centrifugation at 100,000 g of the post-mitochondrial supernatant. The membrane proteins are extracted as indicated above in reference to Table 2 for 30 mins. at 4° C. The respective concentrations of the proteins and detergents are 4 and 15 mg/ml. Following centrifugation, the activity of cytochrome $P-450_{17\alpha}$ is measured in the supernatant by checking the transformation of ($^3$H)-pregnenolone into ($^3$H)-17α-hydroxy-pregnenolone.

TABLE 3

| Detergent | Extraction rate | Inactivation rate |
|---|---|---|
| 1-heptyl-1-thio-α,β-D-glucopyranoside | 85 | 0 |
| 1-octyl-1-thio-α,β-D-glucopyranoside | 93 | 0 |
| 1-octyl-1-thio-β-D-glucopyranoside[a] | 31 | 0 |
| 1-octyl-β-D-glucopyranoside[a] | 89 | 20 |
| 1-heptyl-1-thio-α,β-lactoside | 57 | 0 |
| 1-octyl-1-thio-α,β-lactoside | 65 | 57 |
| 1-octyl-1-thio-α,β-cellobioside | 72 | 0 |
| 1-octyl-1-thio-α,β-maltoside | 58 | 0 |

[a]Commercial products of "ultra-pure" grade.

The Examples below represent typical operating procedures for preparing products of the present invention, and are illustrative of the invention without thereby implying limitation.

EXAMPLE 1

Preparation of 1-octyl-1-thio-$\alpha,\beta$-D-glucopyranoside

The commercial reagent poly-(hydrogen fluoride)-pyridinium (hydrogen-fluoride pyridinium 60-70/30 p/w, Fluka, 10 ml) and 1-octanethiol (1 ml, 5.6 mmoles) are added to 1 g (5.5 mmoles) of D-glucose in a Teflon container. The charge is agitated at ambient temperature using a magnetic stirrer for a minimum time period of 45 mins. The stirring can be performed for as long as up to 5 hours without detriment. Thereafter, diethylether (100 ml) is added and the acidity of the charge is neutralized by the addition of calcium carbonate (5 g) thereto. Next, the mineral salts present are filtered out and the charge concentrated at reduced pressure. The oily residue obtained is dissolved in diethylether (100 ml). This charge is then washed with water (50 ml). The wash waters are then re-extracted using diethylether (2×50 ml). The combined organic charges are dried on sodium sulfate and then concentrated. The 1-octyl-thio-$\alpha,\beta$-D-glucopyranoside so obtained is in the form of an oily product (1.8 g) containing no more than 5% of D-glucose-di-1-octyl-dithioacetal as estimated by the NMR spectrum of $^{13}$C. The same technique provides a rating of 44% of the $\alpha$ anomer proportion for the 1-octyl-1-thio-$\alpha,\beta$-D-glucopyranoside present with the remaining 56% consisting of the $\beta$ anomer.

The D-glucose-di-1-octyl-dithioacetal contaminant is eliminated by crystallization in methanol or ethanol, or by chromatography on a silica gel column (Merck 60, 230-400 mesh) using a volume mixture of 5:1 of chloroform to methanol. With this eluant mixture, the $R_f$ of 1-octyl-1-thio-$\alpha,\beta$-D-glucopyranoside is 0.15 on the silica gel plate (Merck 60, $F_{254}$) and that of its $\beta$ anomer is 0.17. Column chromatography can also be used to separate the anomer mixture if separation is desired. In the applications described herein, however, the total anomer mixture is used. After eliminating the D-glucose-di-1-octyl-dithioacetal, the quantity of 1-octyl-1-thio-$\alpha,\beta$-D-glucopyranoside obtained in the form of an oil is 1.6 g (95%); $[\alpha]_D + 129.2°$ (c 1.62, DMSO).

Analysis of $C_{14}H_{28}O_5S$ as calculated is C=54.5; H=9.0; S=10.4; and as measured is C=54.45; H=9.59; S=10.26. NMR $^{13}$C=(50.323 MHz, CDCl$_3$, $\delta$ ppm related to CDCl$_3$ at 77.2 ppm); anomer $\alpha$: 86.3 (C-1); 74.5, 72.0, 71.3 (C-3, C-2, C-5); 69.2 (C-4); 60.9 (C-6); 31.8, 30.7, 29.90 (2), 29.3, 22.6 (6 CH$_2$); 30.9 (S-CH$_2$); 14.0 (CH$_3$); anomer $\beta$: 85.9 (C-1); 79.6 (C-3); 77.8 (C-5); 72.7 (C-2); 69.4 (C-4); 61.5 (C-6); 31.8, 30.6, 29.90 (2), 29.1, 22.6 (6 CH$_2$); 30.9 (S-CH$_2$); 14.0 (CH$_3$).

EXAMPLE 2

Preparation of 1-octyl-2-acetamido-2-desoxy-1-thio-$\alpha,\beta$-D-glucopyranoside Ten ml of the commercial reagent poly-(hydrogen fluoride)-pyridinium and 0.8 ml (4.5 mmoles) of 1-octanethiol are added at room temperature to 1 g (4.5 mmoles) of 2-acetamido-2-desoxy-D-glucose in a Teflon container. The charge is agitated for 4 hours. The formed 1-octyl-2-acetamido-2-desoxy-1-thio-D-glucopyranoside is then precipitated from the reaction charge by the addition of diethylether, separated by decantation, and washed several times with diethylether. A white powder (1.4 g, 87%) is obtained containing the $\alpha$ and $\beta$ anomers (NMR $^{13}$C) in a relative proportion of 6:4; $[\alpha]_D + 40.3°$ (c 1.0, DMSO).

Analysis of $C_{16}H_{31}O_5NS$ as calculated is C=55.8; H=9.0; N=4.1; S=9.0; and as measured is C=55.7; H=8.89; N=4.0; S=9.0. NMR $^{13}$C=(50.323 MHz, dimethylsulfoxide-d$_6$, $\delta$ ppm relative to (CH$_3$)$_2$ SO at 39.6 ppm); 84.5 (C-1$\beta$), 83.7 (C-1$\alpha$); 81.4, 75.9, 73.7, 71.2(2), 71.0 (C-3, C-4, C-5); 61.7, 61.2 (C-6); 55.03, 54.8 (C-2).

EXAMPLE 3

Preparation of 1-heptyl-1-thio-$\alpha,\beta$-D-glucopyranoside

Five to ten ml of the poly-(hydrogen fluoride)-pyridinium reagent and 0.9 ml (5.6 mmoles) of 1-heptanethiol are added to 1 g (5.55 mmoles) of D-glucose in a Teflon container. The charge is agitated by means of a magnetic stirrer and then processed in the manner of Example 1. Following elimination of the contaminant D-glucose-di-1-heptyl-dithioacetal, 1.4 g (85%) of 1-heptyl-1-thio-$\alpha,\beta$,-D-glucopyranoside is obtained in oil form having a relative proportion of 44:56 of the $\alpha$ to $\beta$ anomers (NMR $^{13}$C): $[\alpha] + 147.3°$ (c 1.2, DMSO).

Analysis of $C_{13}H_{26}O_5S$ as calculated is C=53.1; H=8.8; S=10.9; and as measured is C=53.1; H=9.1; S=10.3. NMR $^{13}$C=(50.323 MHz, CDCl$_3$, $\delta$ ppm in relation to CDCl$_3$ at 77.2 ppm); anomer $\alpha$: 86.8 (C-1); 75.0, 72.3, 71.8, 69.8 (C-2, C-3, C-4, C-5); 61.6 (C-6); anomer $\beta$: 86.4 (C-1); 79.6, 77.8, 72.8, 69.5 (C-2, C-3, C-4, C-5); 61.6 (C-6).

EXAMPLE 4

Preparation of 1-octyl-1-thio-disaccharides derived from cellobiose, lactose and maltose One ml (5.6 mmoles) of 1-octanethiol and 5 ml of the commercial reagent poly-(hydrogen fluoride)-pyridinium are added to 1 g (2.9 mmoles) of cellobiose, lactose or maltose in a Teflon container. The charge is agitated by a magnetic stirrer at room temperature for 1 hour. Thereafter, 180-200 ml of diethylether is added. The precipitate formed is separated by decantation. A new quantity (100 ml) of diethylether is then added, whereupon calcium carbonate is introduced into the charge until the reaction has a neutral pH. Thereafter, the mineral salts are filtered out and the filtrate concentrated under reduced pressure. The oily residue obtained is dissolved in 20 ml of methanol. Adding ether to the methanol charge provides for the precipitation of the corresponding 1-octyl-1-thiodisaccharides which are then separated by filtration or decantation (1.1 g, 80%). The relative proportions of the anomer mixtures are computed by integrating the signal values of $^{13}$C NMR C-6 signals. These spectroscopic results are obtained at 50.123 MHz in dimethylsulfoxide-d$_6$ and the spectrum descriptions below are given in $\delta$ ppm in relation to (CH$_3$)$_2$SO at 72.0 ppm. The products are characterized as follows:

(1) 1-octyl-1-thio-$\alpha,\beta$-cellobioside: $[\alpha]_D + 29.2°$ (c 1.23, DMSO). Analysis of $C_{20}H_{38}O_{10}S$ as calculated is C=51.1; H=8.1; S=6.8; and as measured is C=51.3; H=8.23; S=7.09. $^{13}$C NMR=103.2 (C-1'); 85.0 (C-1 $\alpha$, $\beta$); 61.2 (C-6'); 60.7 (C-6 $\beta$); 60.2 (C-6 $\alpha$); $\alpha/\beta \approx 1:1$;

(2) 1-octyl-thio-$\alpha,\beta$-lactoside: $[\alpha]_D + 46.7°$ (c 1.5, DMSO). Analysis of $C_{20}H_{38}O_{10}S$ as calculated is C=51.1; H=8.1; S=6.8; and as measured is C=51.2; H=8.24; S=70. $^{13}$C NMR=103.6 (C-1'); 84.9 (C-1 $\alpha,\beta$); 60.5 (C-6'); 60.7 (C-6 $\beta$), 60.2 (C-6 $\alpha$); $\alpha/\beta \approx 1:1$; and (3) 1-octyl-1-thio-$\alpha,\beta$-maltoside: $[\alpha]_D + 43°$ (c 1.77 DMSO). Analysis of $C_{20}H_{38}O_{10}S$ as computed is C=51.1; H=8.1; S=6.8; and as measured is C=50.5; H=7.9; S=67. $^{13}$C NMR=101.1 (C-1'); 85.4 (C-1 α,β); 61.3 (C-6 β); 61.0 (C-6 α, C-6').

EXAMPLE 5

Preparation of 1-hexyl-α,β-D-glucopyranoside

Ten ml of the commercial poly-(hydrogen fluoride)-pyridinium reagent and 1.4 ml (12 mmoles) of 1-hexanol are added to 1 g (5.5 mmoles) of D-glucose in a Teflon container. Following magnetic stirring of the mixture at room temperature, 100 ml of diethylether and 20 g of calcium carbonate are added. Thereafter, the insoluble mineral salts present are filtered out and the filtrate concentrated at reduced pressure. The residual oil present is absorbed in the diethylether and the etherfied charge washed with water and dried on sodium sulfate. The 1-hexyl-D-glucopyranoside is obtained by concentration (830 mg, 50%) in the form of an oil containing the α and β anomers in a ratio of 7:3 as estimated by integrating the $^{13}$C NMR signals: [α]$_D$+103.2° (c 1.6 DMSO). $^{13}$C NMR=(50.323 MHz, D$_2$O, δ ppm in relation to hexyl CH$_3$ at δ 14 ppm); β anomer: 102.8 (C-1); 76.7, 76.3, 72.3, 70.5 (C-2 - C-5); 61.6 (C-6); 68.5 (OCH$_2$) 31.3, 29.2, 25.3: 22.4 (4CH$_2$); 14 (CH$_3$); α anomer: 98.7 (C-1); 74.2 (2), 72.2, 70.4 (C-2 C-5); 61.5 (C-6); 68.5 (OCH$_2$); 31.3: 29.2, 25.5: 22.4 (4 CH$_2$); 14 (CH$_3$).

EXAMPLE 6

Preparation of 1-hexyl-α,β-cellobioside

Five ml of commercial reagent poly-(hydrogen fluoride)-pyridinium and 1.4 ml (7.7 mmoles) of hexanol are added to 1 g (2.9 mmoles) of cellobiose in a Teflon container. Following magnetic stirring for one hour at room temperature, 100 ml of diethylether and about 5 g of calcium carbonate are added to the mixture. The mixture is agitated for another hour and then filtered. The salts are washed with 50 ml of methanol. The combined filtrates are concentrated at reduced pressure and any residual pyridine is entrained by co-evaporation with water. The crude reaction product is in the form of an oil (1.23 g) and at this stage contains the 1-hexyl-cellobioside in the form of an anomer mixture α/β=1:1 ($^{13}$C NMR) as well as a small quantity of unreacted cellobiose. The 1-hexyl-cellobioside can be obtained in pure form (620 mg, 50%) by being passed through a resin column DOWEX 1 (OH$^-$) balanced in methanol in the manner described in *Biochemistry* 19, (1980) 4108. $^{13}$C NMR=(50.323 MHz, $^2$H$_2$O, δ ppm in relation to C-6 α at 60.1); 102.9 (C'-1); 98.3 (C-1α); 102.5 (C-1β); 79.4 (C-4); 68.9 (—OCH$_2$—); 61.3 (C'-6); 60.1 (C-6α); 60.8 (C-6 β).

EXAMPLE 7

Preparation of methyl-α,β-cellobioside

Five ml of the commercial reagent poly-(hydrogen fluoride)-pyridinium reagent and 0.22 ml (7 mmoles) of methanol are added to 1 g (2.9 mmoles) of cellobiose in a Teflon container. Following magnetic stirring of the mixture for one hour at room temperature, 100 ml of diethylether and about 5 g of calcium carbonate are added. Next, the mixture is stirred for another hour whereupon the mixture is filtered and the salts washed with 20 ml of methanol. The combined filtrates are concentrated at reduced pressure and any residual pyridine is entrained by co-evaporation with water. The product obtained is 1 g (90%) of oil containing the anomer mixture of methyl-cellobioside α/β=2:3 ($^{13}$C NMR). $^{13}$C NMR=(50.323 MHz), $^2$H$_2$O, δ ppm in relation to C-6 α at 60.80 ppm); 103.9 (C-1 β); 103.3 (C'-1); 99.8 (C-1 α); 61.30 (C'-6); 60.80 (C-6 α,β); 57.6 (-OCH$_3$ β); 55.7 (-OCH$_3$ α).

As will be apparent to one skilled in the art, various modifications can be made within the scope of the aforesaid description. Such modifications being within the ability of one skilled in the art form a part of the present invention and are embraced by the appended claims.

It is claimed:

1. A process of preparing substituted glycosides comprising reacting in the presence of a poly-(hydrogen fluoride)-pyridinium solvent and reagent a saccharide selected from the group consisting of monosaccharides, reducible disaccharides and reducible oligosaccharides with a thiol to produce an alkyl-1-thio-α,β-glycoside or an alcohol to produce an alkyl glycoside.

2. The process of claim 1 wherein said saccharide is a monosaccharide selected from the group consisting of hexoses and pentoses.

3. The process of claim 2 wherein said monosaccharide is D-glucose.

4. The process of claim 2 wherein said monosaccharide is an amino-desoxy-hexose.

5. The process of claim 1 wherein said saccharide is a disaccharide selected from the group consisting of cellobiose, lactose and maltose.

6. The process of claim 1 wherein when said thiol is reacted with said saccharide, the molar ratio of said thiol to said saccharide is between about 1 and 2.

7. The process of claim 6 wherein said molar ratio of said thiol to said saccharide is approximately 1.

8. The process of claim 1 wherein when said alcohol is reacted with said saccharide, the molar ratio of said alcohol to said saccharide is between about 2 and 3.

9. The process of claim 1 wherein the number of carbon atoms present in said thiol is from 5 to 20.

10. The process of claim 1 wherein the number of carbon atoms present in said alcohol is from 5 to 20.

11. The process of claim 1 wherein said alkyl-1-thio-α,β-glycoside produced is present as a mixture of α and β anomers.

12. The process of claim 11 wherein said alkyl of said alkyl-1-thio-α,β-glycoside is a fatty acid chain.

13. The process of claim 12 wherein said alkyl-1-thio-α,β-glycoside produced has nonionic detergent properties which make said glycoside capable of solubilizing, extracting, and reconstituting membrane proteins.

* * * * *